United States Patent [19]
Liu

[11] Patent Number: 5,981,239
[45] Date of Patent: *Nov. 9, 1999

[54] **SYNTHESIS OF OPTICALLY ACTIVE PHENYLALANINE ANALOGS USING *RHODOTORULA GRAMINIS***

[75] Inventor: Weiguo Liu, Buffalo Grove, Ill.

[73] Assignee: Great Lakes Chemical Corp., West Lafayette, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/936,607

[22] Filed: Sep. 24, 1997

[51] Int. Cl.$^6$ .............................. C12P 13/22; C12P 41/00
[52] U.S. Cl. ............................................ 435/108; 435/280
[58] Field of Search ...................... 435/280, 108

[56] References Cited

U.S. PATENT DOCUMENTS

| | | | |
|---|---|---|---|
| 4,434,228 | 2/1984 | Swann | 435/108 |
| 4,436,813 | 3/1984 | Wood et al. | 435/109 |
| 4,562,151 | 12/1985 | Kishore | 435/108 |
| 4,574,117 | 3/1986 | Vollmer et al. | 435/108 |
| 4,584,269 | 4/1986 | Vollmer et al. | 435/108 |
| 4,584,273 | 4/1986 | Finkelman et al. | 435/108 |
| 4,598,047 | 7/1986 | McGuire | 435/108 |
| 4,600,692 | 7/1986 | Wood et al. | 435/108 |
| 4,636,466 | 1/1987 | McGuire et al. | 435/108 |
| 4,728,611 | 3/1988 | Wood et al. | 435/108 |
| 4,732,851 | 3/1988 | Wood et al. | 435/43 |
| 4,757,015 | 7/1988 | Orndorff et al. | 435/108 |

FOREIGN PATENT DOCUMENTS

| | | |
|---|---|---|
| 897889 | 9/1983 | Belgium . |
| 167411 | 8/1986 | European Pat. Off. . |
| 56-26197 | 3/1981 | Japan . |
| 60-43393 | 3/1985 | Japan . |
| 61-43993 | 3/1986 | Japan . |
| 63-148992 | 6/1988 | Japan . |
| 6113870 | 4/1994 | Japan . |
| 8802024 | 3/1988 | WIPO . |
| 9307279 | 4/1993 | WIPO . |

OTHER PUBLICATIONS

D.S. Hodgins, "Purification, Properties, and the Identification of Catalytically Essential Dehydroalanine," J. of Biological Chemistry, vol. 246, No. 9, pp. 2977–2985 (1971).

G.B. D'Cunha, V. Satyanarayan, and P.M. Nair, "Stabilization of phenylalanine Ammonia Lyase containing *Rhodotorula glutinis* Cells for the Continuous Synthesis of L–Phenylanine Methyl Ester/96/," Enzyme and Microbial Technology, vol. 19, pp. 421–427 (1996).

D.G. Rees and D.H. Jones, "Stability of L–Phenylalanine Ammonia–Lyase in Aqueous Solution and as the Solid State in Air and Organic Solvents," Enzyme and Microbial Technology, vol. 19, pp. 282–288 (1996).

C.T. Evans, C. Choma, W. Peterson, and M. Misawa, "BioConversion of Trans–Cinnamic Acid to L–Phenylalanine in an Immobilized Whole Cell Reactor," Biotechnology and Bioengineering, vol. 30, pp. 1067–1072 (1987).

K. Nakamichi, K. Nake, S. Yamada, and I. Chibata, "Induction and Stabilization of L–Phenylalanine Ammonia–Lyase Activity in *Rhodotorula glutinis*," Applied Microbiology and Biotechnology, vol. 18, pp. 158–162 (1983).

Renard et al., Biotechnology Letters, vol. 14, No. 8 (Aug. 1992) pp. 673–678.

*Primary Examiner*—Sandra E. Saucier
*Attorney, Agent, or Firm*—Fitzpatrick, Cella, Harper & Scinto

[57] ABSTRACT

A biocatalytic process to produce optically active phenylalanine analogs from arylacrylic acids is disclosed in which *Rhodotorula graminis* yeast containing phenylalanine ammonia-lyase introduces a molecule of ammonia stereoselectively onto the double bond of a 3-substituted acrylic acid. The substituent at the 3-position of the 3-substituted acrylic acid includes, for example, aromatic rings such as substituted phenyl groups, five member aromatic heterocyclics, and six member aromatic heterocyclics.

15 Claims, No Drawings

SYNTHESIS OF OPTICALLY ACTIVE PHENYLALANINE ANALOGS USING *RHODOTORULA GRAMINIS*

BACKGROUND OF THE INVENTION

1. Field of the Invention

The present invention relates to a biocatalytic process to produce optically active phenylalanine analogs from arylacrylic acids. In this process yeast containing L-phenylalanine ammonia lyase ("PAL") introduce a molecule of ammonia stereoselectively onto the double bond of a 3-substituted acrylic acid. The substituent at the 3 position of the 3-substituted acrylic acid is an aryl substituent including, for example, substituted phenyl groups, five member aromatic heterocyclics, and six member aromatic heterocyclics. In particular, this invention relates to a process for preparing phenylalanine-like aromatic amino acids using phenylalanine ammonia-lyase containing yeast, *Rhodotorula graminis* ATCC 20804.

2. Related Background Art

Phenylalanine and its derivatives have been used as essential building blocks in the construction of various types of biologically active molecules. An extremely important and powerful class of pharmaceutical compounds called protease inhibitors contain a phenylalanine-like architecture as their pharmacophores. These protease inhibitor drugs, especially HIV-protease inhibitors are appearing in increasing numbers in pharmacies and hospitals. The three recently approved protease-inhibitor drugs for treatment of AIDS all incorporate a phenylalanine derived moiety in their chemical structures. The search for more potent and effective protease inhibitors is continuing not only in the treatment of HIV infections but also in other disease area such as influenza and human cytomegalovirus (CMV). Currently, there is a pressing need for a general process of preparing a variety of optically active unnatural amino acids having phenylalanine-like structures as chiral synthons for synthesis of these drug candidates.

Although phenylalanine can be readily prepared in large scales by various existing methods including chemical and biological transformations, its analogs with various substitutions on the aromatic ring or with different aromatic ring systems such as naphthyl and heterocyclic ring systems, have been much more difficult to synthesize.

Trans-cinnamic acid ("t-cinnamic acid") and ammonia reversibly forms L-phenylalanine through the addition of the amino group ("amination") to the double bond of t-cinnamic acid. Elimination of ammonium ions from phenylalanine is called "deamination". The reaction is catalyzed by Phenylalanine Ammonia-Lyase (PAL) in either direction. Examples in the prior art of use and production of PAL, and of methods to produce phenylalanine with the assistance of PAL, include the references below.

U.S. Pat. No. 4,584,273, Finkelman et al., herein incorporated by reference in its entirety, discloses a method for the production of PAL by fermentation.

U.S. Pat. No. 4,598,047, McGuire, herein incorporated by reference in its entirety, discloses a method for producing catabolite resistant, PAL-producing mutant bacteria and yeast. The PAL thus produced is disclosed as being usable to make L-phenylalanine.

Hodgins, D., *Journal of Biological Chemistry*, 1971, 2977–2985, herein incorporated by reference in its entirety, reports on PAL purified from *Rhodotorula glutinis*, and the inhibiting effects of various ring-substituted analogues on phenylalanine deamination.

D'Cunha, G., Satyanarayan, V., and Nair, P., *Enzyme and Microbial Technology*, 1996, 421–427, herein incorporated by reference in its entirety, reports a procedure for the direct one-step synthesis of L-phenylalanine methyl ester by using PAL.

Rees, D., and Jones, D., *Enzyme and Microbial Technology*, 1996, 282–288, herein incorporated by reference in its entirety, reports producing PAL from *Rhodosporidium toruloides*. The stability of the PAL was also studied.

Evans, C., Choma, C., Peterson, W., and Misawa, M., *Biotechnology and Bioengineering*, 1996, 282–288, herein incorporated by reference in its entirety, reports the use of immobilized cells from a PAL-containing yeast mutant FP10M6 derived from *rhodotorula rubra* to demonstrate the feasibility of a continuous process of L-phenylalanine production from t-cinnamic acid.

Nakamichi, K., Nabe, K., Yamada, S., and Chibata, I., *European Journal of Applied Biotechnology*, 1983, 158–162, herein incorporated by reference in its entirety, reports the effect of various amino acids such as D-phenylalanine, D and L isoleucine, D and L leucine, L-valine, L-methionine, L-tryptophan, and L-tyrosine on the PAL activity in *Rhodotorula glutinis*.

U.S. Pat. No. 4,574,117, Vollmer et al., herein incorporated by reference in its entirety, discloses a method for producing L-phenylalanine from t-cinnamic acid and ammonia or ammonium salts using PAL as a catalyst. Reducing agents such as hydrogen sulfide, thioglycolic acid, thiosulfuric acid, nitrous acid, sulfurous acid, ammonium and metal salts of the above, dithiothreitol, ethylmercaptan, ethylenemercaptan, methylmercaptan, 2-mercaptoethanol, hydrogen, nitrous oxide, iron (II) compounds, manganese (II) compounds, sulfur, and zinc are added to the bioreaction mixture to reduce the effects of oxygen on catalyst life.

U.S. Pat. No. 4,584,269, Vollmer et al., herein incorporated by reference in its entirety, discloses a method for the PAL enzymatic conversion of t-cinnamic acid and ammonia to L-phenylalanine under substantially anaerobic, static conditions.

U.S. Pat. No. 4,562,151, Kishore, herein incorporated by reference in its entirety, discloses a method for producing L-phenylalanines and analogues from t-cinnamate and ammonia with the use of polyhydric alcohols to enhance instantaneous rates of reaction and to inhibit inactivation of the enzyme.

U.S. Pat. No. 4,757,015, Orndorff, herein incorporated by reference in its entirety, discloses a method for producing phenylalanine from t-cinnamate and ammonia with the use of *Rhodotorula graminis* ATCC 20804.

JP 06113870 A2, describes a procedure for the direct one-step enzymatic conversion of trans-cinnamyl methyl ester to L-phenylalanine methyl ester. The reverse reaction of phenylalanine ammonia lyase from *Rhodotorula glutinis* was utilized for this conversion.

JP 60043393 A, describes production of L-phenylalanine (LPA) by reacting cinnamic acid with ammonia or an ammonia-releasing substance in an aqueous medium in presence of a culture bath, cells or their processed material from a microorganism having L-phenylalanine ammonia lyase activity. The microorganism includes *Rhodotorula rubra* ATCC 20258, *Rhodotorula texensis* IFO 932, *Rhodotorula glutinis* IFO 0559, and Sporobolomyces IFO 1040.

JP 61043993 A, describes catalyzed formation of alpha-amino acids from 2-en-carboxylic acids and excess $NH_3$ reacted in $H_2O$ under anaerobic conditions in the presence of ammonia-lyase or mycelia such as *Sporobolomyces roseus* IF01040 containing ammonia-lyase or a substance derived from ammonia-lyase.

JP 06113870 A, describes the preparation of beta-substituted alanine derivatives of formula R—CH$_2$—CH(NH$_2$)—CO$_2$H, comprising the reaction of ammonia with the acrylic acid derivative of formula R—CH=CHCO$_2$H in the presence of L-phenyl alanine ammonia-lyase. In the formulae, R is a monovalent group derived from a heterocyclic compound. Preferably, R=pyridyl, furyl or thienyl. Suitable enzymes include one or a mixture of the bacterial body obtained by culturing the transformant of *Escherichia coli*, MT10243 (FERM P-9023), integrated with the gene of the L-phenyl alanine ammonia-lyase originating from Rhodosporidium L-phenyl alanine ammonia-lyase producing bacterium (bacteria), treated products of the bacterial body, such as the washed, dried, crushed and fixed product, and purified enzyme extracted from the body or products.

A great volume of research is devoted to the application of PAL, as shown by the references above. Much work has been done with prokaryotic vectors to derive PAL catalysis of the cinnamic acid/phenylalanine reaction. Several eukaryotic yeast derived PAL have been used to catalyze the formation of phenylalanine. However, few yeast derived PAL have been used to produce a variety of optically active unnatural amino acids having phenylalanine-like structures as chiral synthons for synthesis. In particular, *Rhodotorula graminis* ATCC 20804 expressed PAL has not been used to introduce a molecule of ammonia stereospecifically into the double bond of the composition,

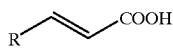

to generate the optically active amino acid of the composition,

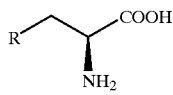

wherein R is a substituted aromatic six-member ring system or a six or five-membered heterocyclic ring system including single and multiple substituted analogs.

SUMMARY OF THE INVENTION

The present invention is a general and practical Chemo-Enzymatic process for preparation of phenylalanine analogs. In particular, the process involves the introduction of a molecule of ammonia stereospecifically into the double bond of the composition,

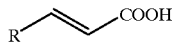

or a salt thereof to generate the optically active amino acid of the composition,

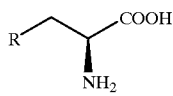

or a salt thereof
wherein R is (i) a substituted or unsubstituted aromatic six-member ring system, (ii) a substituted or unsubstituted aromatic five-membered ring system, or (iii) a substituted or unsubstituted bicyclic aromatic ring system, and wherein said aromatic six-member ring system is not unsubstituted phenyl.

The stereo specific introduction of ammonia is accomplished through the use of microorganism cells, more specifically, the cells of the yeast strain *Rhodotorula graminis* ATCC 20804 as the biocatalyst for the stereospecific conversion. Several yeast strains containing phenylalanine ammonia-lyase were screened on a small scale for their ability to introduce a molecule of ammonia stereoselectively onto the double bond of a 3-substituted acrylic acid. Phenylalanine ammonia-lyases from *Rhodotorula graminis* ATCC 20804 was found to demonstrate the broadest substrate specificities. Cells of *Rhodotorula graminis* was obtained from American Type Culture Collection as ATCC 20804, and maintained in 20% glycerol under −70° C.

The process of the present invention may be carried out by combining phenylalanine ammonia-lyase from *Rhodotorula graminis* with a composition represented by the formula,

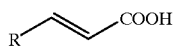

to generate the optically active amino acid represented by the formula,

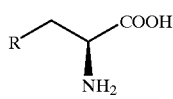

wherein R as previously described.

Another embodiment of the present invention is directed to carrying out the process by incubating *Rhodotorula graminis* cells in a substrate containing a composition represented by the formula,

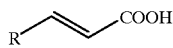

wherein R is as previously described and an effective amount of ammonia to generate the optically active amino acid represented by the formula,

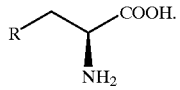

DETAILED DESCRIPTION OF THE INVENTION

The process of this invention is directed to combining phenylalanine ammonia-lyases from *Rhodotorula graminis* ATCC 20804 with the composition,

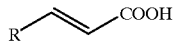

to generate the optically active amino acid of the composition,

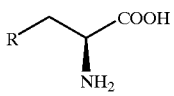

wherein R is (i) a substituted or unsubstituted aromatic six-member ring system, (ii) a substituted or unsubstituted aromatic five-membered ring system or (iii) a substituted or unsubstituted bicyclic aromatic ring system, and wherein said aromatic six-member ring system is not unsubstituted phenyl. The ring system may be heterocyclic. Such heterocycles may include up to four heteroatoms in each ring of the ring system. The heteroatoms are typically selected from nitrogen, oxygen, sulfur or mixtures thereof. The substituted ring systems may be singly or multiply substituted. Exemplary substituents include halo, alkyl, amino, nitro, cyano, and hydroxyl groups.

Cells of *Rhodotorula graminis* were obtained from American Type Culture Collection as ATCC 20804, and maintained in 20% glycerol under −70° C.

Exemplary conditions used in the process of the present invention are described below.

The general protocol for the biocatalytical production and bioconversion according to the present invention may be preferred in several steps. The *Rhodotorula graminis* ATCC 20804 is grown at step 1. The cultures are then fermented in step 2. When, and if, the initial glucose level drops below a set level, additional glucose is added at step 3. Subsequent additions of glucose are possible. The fermenter contents are harvested in step 4. Step 5 is the biotransformation step in which *Rhodotorula graminis* ATCC 20804 cells are suspended in the substrate solution along with the acrylic acid starting material and ammonia. Typically this step includes incubation under nitrogen. In step 6 a supernatant is obtained generally by centrifuging the contents from step 5, and concentrating the supernatant to small volume. This is typically followed by mixing with alcohol, filtering, and concentrating the filtrate. Lastly, step 7 is the collection of the product and purification. Typically this is accomplished by methods such as recrystallization or various chromatographic procedures such as thin layer chromatography (TLC) and high performance liquid chromatography (HPLC). The *Rhodotorula graminis* cells can be induced with leucine or isoleucine.

Production of Biocatalyst

The yeast strain *Rhodotorula graminis* ATCC 20804 was grown in a media which comprised PAL seed medium, 10 g/L nutritional feed Amberex 695 AYE 4, a type of yeast extract (made by Red Star Bioproducts, Juneau, Wis.), log/L Glucose, and 0.1 ml/L MAZU DF 204 (made by PPG Industries Inc., Gurnee, Ill.) antifoaming agent. The pH was adjusted to 6.1 with 45% KOH.

The PAL Fermentation medium comprised 5 g/L Amberex 695, 2 g/L $(NH_4)_2HPO_4$, 14 g/L Glucose, 9 g/L L-phenylalanine, and 0.1 ml/L MAZU DF 204 antifoaming agent. The pH was 6.0.

Seed Growth preparation of 1 growth tube per Fernbach culture flask (Fernbox): The yeast strain ATCC 20804 was taken from cryo-vials and spread on a petri dish containing nutrient agar. The petri dish was incubated at 30° C. for 24–72 hours to obtain colonies. A capped growth tube containing 10 mL of PAL seed medium was inoculated with an isolated single colony, and incubated at 30° C. in a shaker under 250 rpm for 24 hours. A Fernbach culture flask containing 1000 mL of PAL seed medium was inoculated with 10 mL of culture from the growth tube, and incubated at 30° C. in a shaker under 250 rpm for 24 hours. Cultures were checked for contamination under a microscope.

Fermentation (20 L)

Next, fermentation was performed. The pre-inoculation volume level was 15 L, and comprised 75 g/L Amberex 695, 30 g $(NH_4)_2HPO_4$, 210 g Glucose, 135 g L-phenylalanine, and 1.5 g MAZU DF 204 antifoaming agent, at a pH of 6.0. The inoculation was 10% (1.5 L). The pH set point was 6.0 (controlled with the addition of ammonia or 25% sulfuric acid). Air flow was 1 vvm, 15 slpm. Mixing was at 800 rpm. The temperature was 30° C.

Additions

After fermentation was initiated, additional glucose was added. Two additions were made. When the initial glucose level dropped below 1 g/L, additional glucose was added until a level of 12 g/L was reached. When the glucose level dropped again below 1 g/L, 600 mL of 25% Amberex 695 and 36 g (2 g/L) L-isoleucine was added.

The run time was 24 hours and the final pH was 10.86.

Harvest

The contents from each fermenter were concentrated to 1.0 L through ultrafiltration, washed with water, and then centrifuged at 5000 rpm to obtain the cell pellet of approximately 0.25 gram dry cell per gram of pellet. The cells could be stored at −70° C. for several months without losing activity.

Biotransformation

In a typical example, the 3-substituted acrylic acid starting material was dissolved in 10% (Wt/Wt) aqueous ammonia (pH=10.5, adjusted by addition of concentrated sulfuric acid) to obtain a solution with approximately 20–50 g/L substrate concentration. The concentration of ammonia may range from about 5 wt. & to about 45 wt. % of the aqueous solution. The preferred range is from about 10 wt. % to about 30 wt. % of the aqueous solution. Other solvent systems can be used, as can be easily determined by one of ordinary skill in the art for specific acrylic acid starting material that are not sufficiently soluble in 10% aqueous ammonia. "Sufficiently soluble" as used in this case is a solubility that effectively leads to sufficient solubilization of the starting material to produce a yield of product. Exemplary other solvent systems for substrates that are not sufficiently soluble in 10% aqueous ammonia include aqueous ammonia with additional co-solvents such as dimethylformaldehyde (DMF), tetrahydrofuran (THF), and acetonitrile (MeCN), or with added solubilization agents or detergents such as Triton X100 (made by Aldrich Chemical Company, Inc., Milwaukee, Wis.), Tween-80 (made by Aldrich Chemical Company, Inc., Milwaukee, Wis.), and polyethylene glycol (PEG).

i Rhodotorula graminiscells (about 25 gram dry cell per liter) were suspended in the substrate solution, and the mixture was incubated under nitrogen at 30° C. and mixed at 500 rpm for 48 hours. Cells were then removed by centrifugation. The supernatant was concentrated under vacuum to small volume, mixed with 3× volume of ethanol or methanol, and filtered. The filtrate was concentrated and allowed to stand in a cold room overnight. The product was collected by filtration and further identified and purified by methods such as recrystallization, ion-exchange chromatography, or other known purification or analytical methods.

As a general example of the wide range of substituents available for a particular solvent used in the present invention, the results when 10% aqueous ammonia was used is shown below. The left column tabulates the R substituent of the 3-substituted acrylic acid, the center column tabulates the conversion percent measured, and the right column tabulates the enantiomeric excess percent which is a measure of the enantiomeric purity of the product. In comparison, the unsubstituted cinnamic acid under the same conditions gave an 85% conversion and greater than 99% enantiomeric excess.

| R | Conversion % | Enantiomeric Excess % |
|---|---|---|
| 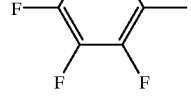 pentafluorophenyl | 80 | >99 |
| 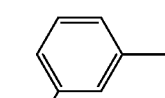 3-chlorophenyl | 80 | >99 |
| 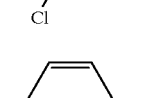 2-chlorophenyl | 80 | >99 |
| 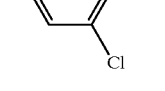 4-chlorophenyl | — | — |
| 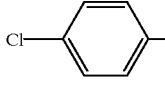 3,4-dichlorophenyl | — | — |
| 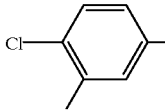 2,6-dichlorophenyl | 24 | >99 |
| 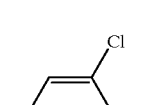 2,4,6-trichlorophenyl | — | — |
| 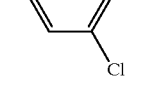 3-bromophenyl | 80 | >99 |
| 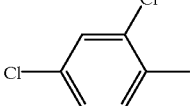 4-bromophenyl | — | — |

-continued

| R | Conversion % | Enantiomeric Excess % |
|---|---|---|
|  3-fluorophenyl | 80 | >99 |
| 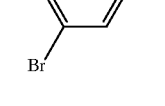 2-fluorophenyl | 80 | >99 |
|  4-fluorophenyl | 80 | >99 |
|  4-methylphenyl | — | — |
|  4-formylphenyl | — | — |
| 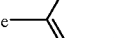 4-aminophenyl | — | — |
| 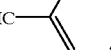 2-nitrophenyl | 45 | >99 |
| 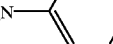 3-nitrophenyl | 45 | >99 |
|  4-nitrophenyl | — | — |
| 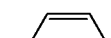 3-cyanophenyl | 80 | >99 |
|  4-cyanophenyl | 20 | >99 |
|  3-hydroxyphenyl | 80 | >99 |

-continued

| R | Conversion % | Enantiomeric Excess % |
|---|---|---|
| 2-hydroxyphenyl | decomposed | — |
| 4-hydroxyphenyl | 30 | >99 |
| 1-naphthyl | 10 | >99 |
| 2-naphthyl | — | — |
| 2-thienyl | 80 | >99 |
| 2-furyl | — | — |
| 3-pyridyl | 87 | >99 |

As can be seen, certain substituted aromatic ring substituents were not detected in the reaction product. For example, cinnamic acid derivatives with para-substitutions on the aromatic ring such as 4-bromo, 4-chloro, 4-formyl, 4-nitro, 3,4-dichloro, 4-methyl, and 2,4-dichloro cinnamic acids did not respond to the biocatalyst under the specific reaction conditions tried with 10% aqueous ammonia, while other para-substituted cinnamic acids such as 4-cyano, 4-hydroxyl, and 4-fluoro cinnamic acids did respond to the enzyme system to give the corresponding phenylalanine analogs in good yield. While not bound by the theory, it is believed that this difference in activity can be explained by the differences in the solubility of the substrates in the solvent system applied to the bioconversion reactions. The first group of the para-substituted substrates are far less soluble in the 10% aqueous ammonia used to perform the biocatalytic reactions, while the second group are all soluble. That is, the first group was insufficiently soluble.

Accordingly, solubilization of such insufficiently soluble substituted cinnamic acids in a solvent system that is compatible with the biotransformation conditions would result in appreciable conversion to the corresponding amino acid products. It is believed that such solvent systems for improving solubility of the substrates that were insufficiently soluble in aqueous ammonia can be obtained by the addition of co-solvents such as dimethylformaldehyde (DMF), tetrahydrofuran (THF), and acetonitrile (MeCN), or with the introduction of solubilization agents or detergents such as Triton X100, Tween-80, and polyethylene glycol (PEG).

For example, it was found that the addition of 10% PEG-800 to the bioconversion mixture of *Rhodotorula graminis* cells with 3-(2-naphthyl)acrylic acid, which is almost insoluble without PEG, increased the yield of 2-naphthylalanine product from undetectable to about 10%.

Further, while not bound by the theory, it is believed that the 2-phenol substituent gave a product that decomposed subsequent to its formation. It is believed that a less basic solvent system would lead to the product's recovery.

The Examples which follow are intended as an illustration of certain preferred embodiments of the invention, and no limitation of the invention is implied.

EXAMPLES

Example 1

Synthesis of 3-(S)-pyridylalanine from 3-pyridylacrylic acid

In a 2.0 L fermentor, 50 g of 3-pyridylacrylic acid was dissolved in 1.0 L of 10% (Wt/Wt) aqueous ammonium hydroxide. The solution was adjusted to pH=10 with concentrated sulfuric acid and purged with nitrogen for 30 minutes. Fresh cells of *Rhodotorula graminis* ATCC 20804 (100 g wet cells, equivalent to 25 g dry cells) were added. The mixture was stirred at 30° C., at 500 rpm, under a blanket of nitrogen for 48 hours.

About 1.0 mL of the suspension was taken and centrifuged at 2000 rpm for 2 minutes. The supernatant was spotted on a silica gel TLC plate, developed with a solvent system of chloroform/methanol/water/formic acid with a ratio (Vol/Vol/Vol) of 60:40:8:2. The developed TLC plate was sprayed with a 0.2% (Wt/Wt) ninhydrin solution in ethanol and baked in a 100° C. oven for 5 minutes.

The TLC result indicated that most of the starting material had been converted to an amino acid product. The reaction mixture was then centrifuged at 5000 rpm for 30 minutes. The supernatant was concentrated under vacuum to a volume of about 200 mL. The remaining solution was adjusted to pH 5.8 with 2.5N sulfuric acid, followed by addition of 500 mL of anhydrous ethanol. The resulting suspension was stirred at room temperature for 2 hours and filtered. The filtrate was concentrated under vacuum to about 200 mL and a sample of the solution was taken for measuring the water content. Fresh anhydrous ethanol was added and concentration of the solution was continued until the water content of the solution was below 1% by weight. The final volume of the solution was about 200 mL.

The mixture was cooled in an ice bath with stirring, and gaseous HCl was bubbled in until no more precipitate was produced. The mixture was continuously stirred at 0° C. for two more hours and filtered. The solid was recrystallized in methanol to obtain 22 g of 3-(S)-pyridylalanine dihydrochloride: mp, 234–238° C.; $[\alpha]D_{20}$ −20° 9c 1, ($H_2O$) , 1H NMR ($D_2O$) : d 8.45 (1H, dd, J=2.0, 5.4), 8.40 (1H, m), 7.82 (1H, m), 7.48 (1H, m), 4.06 (1H, dd, J=6.0, 7.5), 3.32 (1H, dd, J=6.0, 14) 3.25 (1H, dd, J=7.5, 14.5).

Example 2

Formation of Pyridylalanine from Different Concentrations of Pyridylacrylic Acid as Substrate A total of 3.0 g of wet cells of ATCC 20804 was suspended in 15 mL of 10% aqueous ammonium hydroxide solution (previously adjusted to pH=10 with concentrated sulfuric acid and purged with nitrogen for 30 minutes). A volume of 5.0 mL of the cell suspension was added to each of three reaction vials containing respectively 100 mg, 250 mg and 500 mg of pyridylacrylic acid.

The above three reaction mixtures with substrate concentration of 20, 50, and 100 mg/mL respectively, were incubated in a shaker at 30° C., and 200 rpm. Samples of 0.2 mL were taken from each of the three reaction vials at incremental time intervals, and centrifuged at 2000 rpm for 2 minutes. The supernatants were taken, and diluted as follows:

Vial #1 (20 mg/mL), 0.1 mL supernatant was added to 0.9 mL of water, dilution factor 10.

Vial #2 (50 mg/mL), 0.05 mL supernatant was added to 0.95 mL of water, dilution factor 20.

Vial #3 (100 mg/mL, 0.02 mL supernatant was added to 0.98 mL of water, dilution factor 50.

The above sample solutions were injected in a high performance liquid chromatograph (HPLC) for quantification of pyridylalanine products. The results are tabulated in Table 1.

TABLE 1

| Substrate | Time (h) | | | | | | | | | |
|---|---|---|---|---|---|---|---|---|---|---|
| | 1 | 3 | 5 | 7 | 22 | 25 | 30 | 52 | 74 | 93 |
| | | | | | Product (g/L) | | | | | |
| 20 mg/mL | 2.45 | 6.77 | 9.49 | 11.58 | 16.21 | 16.35 | 16.83 | 16.91 | 16.51 | 16.40 |
| 50 MG/mL | 2.87 | 9.14 | 13.70 | 16.84 | 27.27 | 27.86 | 27.95 | 28.60 | 28.52 | 28.74 |
| 100 mg/mL | 2.58 | 8.27 | 12.58 | 15.43 | 24.74 | 25.18 | 25.77 | 25.69 | 25.77 | 25.73 |

Example 3
Preparation of Pyridylalanine from Pyridylacrylic Acid Using Cells Grown with or Without Leucine as an Inducer Cells of *Rhodotorula graminis* ATCC 20804 were grown with and without leucine as an inducer using the following standard two-stage protocol:

For non-induction experiments, a medium containing 1.0% yeast extracts, 1.0% peptone, 0.5% $K_2PO_4$, and 0.5% L-phenylalanine in distilled water was prepared in a proper shake flask. The solution was adjusted to pH=8.0 with either 10% NaOH or 6N $H_2SO_4$, sterilized, and inoculated with cells of *Rhodotorula graminis* ATCC 20804. The culture was shaken under 200 rpm at 30° C. for 48 h. A volume of 1% of the stage 1 culture was inoculated to the fresh stage 2 medium and incubation was continued under the same conditions for 24 hours. The cells were then harvested and stored following the same procedure as recited herein above.

For the induction experiment: stage 1 cultures were grown under the same conditions and in the medium as in the non-induction experiment, while the stage 2 medium consists of the following: 1.0% yeast extracts, 1.0% peptone, 0.5% $K_2PO_4$, 0.5% L-phenylalanine, 0.15% leucine, pH=8.0. Induced cells were harvested and stored following the procedure described herein previously.

A total of 1.0 g (wet) of each non-induced and induced cells of *Rhodotorula graminis* ATCC 20804 were suspended in 5 mL of 10% aqueous ammonium hydroxide solution (previously adjusted to pH=10 with concentrated sulfuric acid and purged with nitrogen for 30 minutes). An amount of 250 mg of pyridylacrylic acid was added to each cell suspension and the mixtures were then incubated in a shaker at 30° C., and 200 rpm. Samples of 0.2 mL were taken from each reaction vial at incremental time intervals, and centrifuged at 2000 rpm for 2 minutes.

After sampling at 47 hours incubation, 500 mg of fresh cells of both non-induced and induced *Rhodotorula graminis* ATCC 20804 was added to the reaction mixture and the incubation and sampling were continued. The supernatants were taken, and diluted as follows: From each Vial #1 and Vial #2 (50 mg/mL), 0.02 mL supernatant was taken and added to 0.98 mL of water, to yield a dilution factor of 50.

The above sample solutions were each injected in a HPLC for quantification of pyridylalanine products. The results are shown in Table 2. Inducing with isoleucine would yield similar results.

TABLE 2

| Experiment | Time (h) | | | | | | | | | |
|---|---|---|---|---|---|---|---|---|---|---|
| | 1 | 4 | 6 | 22 | 27 | 30 | 47 | 48 | 54 | 71 |
| | | | | | Product (g/L) | | | | | |
| non-induction | 1.74 | 13.20 | 17.60 | 29.22 | 29.92 | 29.17 | 30.57 | 28.72 | 30.60 | 31.96 |
| induction | 2.66 | 6.63 | 8.82 | 18.30 | 20.27 | 21.34 | 23.16 | 21.89 | 23.99 | 26.47 |

Example 4
Effects of Ammonia Concentration of the Bioconversion of Pyridylacrylic acid To reaction vials containing 100 mg of pyridylacrylic acid and 1.0 g (wet) of cells of *Rhodotorula graminis* ATCC 20804, was added respectively the following:

(A), 5 mL of 10% (Wt/Wt) aqueous ammonium hydroxide solution (previously adjusted to pH=10 with concentrated sulfuric acid and purged with nitrogen for 30 minutes); and (B), 5 mL of concentrated aqueous ammonium hydroxide solution (approximately 30% Wt/Wt ammonia).

100 mL of concentrated aqueous ammonium hydroxide solution (approximately 30% Wt/Wt ammonia) was added to a separate pressure bottle containing 2.0 g pyridylacrylic acid and 20 g (wet) of cells of *Rhodotorula graminis* ATCC 20804 and pressurized with ammonia gas at 40 psi.

The above reaction mixtures were stirred at room temperature (about 20° C). Samples of 0.2 mL were taken from each reaction vial at incremental time intervals, and centrifuged at 2000 rpm for 2 minutes. An accurate volume of 0.1 mL of each supernatant were taken, diluted with 0.9 mL of water and injected in a HPLC for quantification of pyridylalanine products. The results are shown in Table 3.

TABLE 3

| Experiment | Time (h) | | | | | | | |
|---|---|---|---|---|---|---|---|---|
| | 2 | 4 | 7 | 23 | 27 | 32 | 47 | 72 |
| | Product (g/L) | | | | | | | |
| 10% $NH_3$ | 6.04 | 10.77 | 13.80 | 15.78 | 15.81 | 15.59 | 15.79 | 15.85 |
| Conc. $NH_3$ | 5.66 | 8.44 | 10.25 | 11.73 | 12.12 | 12.01 | 12.21 | 12.91 |
| 40 psi $NH_3$ | 0.56 | 0.57 | 0.50 | 0.63 | 0.62 | 0.58 | 0.63 | 0.60 |

Example 5
Effects of Temperature on the Bioconversion of Pyridylacrylic Acid

A solution of 20 mg/mL of pyridylacrylic acid in 10% aqueous ammonium hydroxide was prepared by dissolving 600 mg of the substrate in 20 mL of distilled water followed by the addition of 10 mL of concentrated (30%) ammonium hydroxide. The mixture was adjusted to pH 10 with dropwise addition of concentrated sulfuric acid. A total of 6.0 (wet) cells of *Rhodotorula graminis* ATCC 20804 was added, and the suspension was equally divided into six fractions each containing 5.0 mL of volume.

The reaction mixtures were incubated respectively at 20, 25, 30 35, 40, and 45° C. under 200 rpm for 5 hours. Samples of 0.2 mL volume were taken from each reaction mixture, and centrifuged at 2000 rpm for 2 minutes. Accurate volumes of 0.1 mL of each supernatants were taken, diluted with 0.9 mL of water, and injected in a HPLC for quantification of pyridylalanine products. Relative activities of the biocatalyst at different temperatures were calculated as the percentage of pyridylalanine product relative to that produced at 30° C. The calculated relative activities are shown in Table 4.

TABLE 4

| Temperature (° C.) | 20 | 25 | 30 | 35 | 40 | 45 |
|---|---|---|---|---|---|---|
| Rel Activity (%) | 68 | 74 | 100 | 61 | 49 | 38 |

Example 6
Synthesis of 3-(2-Thienyl)-L-alanine from 3-(2-thienyl) acrylic acid

In a 2.0 L fermentor, 50 g of 3-(2-thienyl)acrylic acid was dissolved in 1.0 L of 10% aqueous ammonium hydroxide. The solution was adjusted to pH=10 with concentrated sulfuric acid and purged with nitrogen for 30 minutes. Thawed cells of *Rhodotorula graminis* ATCC 20804 (100 g wet cells, equivalent to 25 g dry dells) were added. The mixture was stirred at 30° C. and 500 rpm under a blanket of nitrogen for 48 hours. About 1.0 mL of the suspension was taken, centrifuged at 2000 rpm of 2 minutes. The supernatant was spotted on silica gel TLC plate, developed with a solvent system of chloroform/methanol/water/formic acid having a (Vol/Vol/Vol/Vol) of (60:40:8:2). The developed TlC plate was sprayed with a 0.2% ninhydrin solution in ethanol and baked in a 100° C. oven for 5 minutes. The TLC result indicated that most of the starting material had been converted to an amino acid product. The reaction mixture was then centrifuged at 5000 rpm for 30 minutes. The supernatant was concentrated under vacuum to remove ammonia until pH 7, and then passed through a column of strong cation exchange resins (Dowex 50WX8-100, 200 g). The column was then washed with methanol. The methanol eluent was concentrated to a small volume and displaced with anhydrous ethanol.

The ethanol solution was concentrated to about 150 mL and allowed to stand at 4° C. overnight and filtered to obtain 34 g of 3-(2-Thienyl)-L-alanine: 1H NMR ($D_2O$) δ 7.82 (1H,m), 7.45 (1H,m), 7.08 (1H,m), 4.12 (1H,m), 3.25 (2H, m).

Example 7
Synthesis of L-3-fluorophenylalanine from 3-fluorocinnamic acid

In a 1.0 L shake flask, 10 g of 3-fluorocinnamic acid was dissolved in 200 mL of 10% aqueous ammonium hydroxide. The solution was adjusted to pH=10 with concentrated sulfuric acid and purged with nitrogen for 30 minutes. Thawed cells of *Rhodotorula graminis* ATCC 20804 (40 g wet cells, equivalent to 10 g dry cells) were added. The flask was sealed and shaken at 30° C. and 500 rpm under a blanket of nitrogen for 24 hours. About 1.0 mL of the suspension was taken and centrifuged at 2000 rpm of 2 minutes. The supernatant was spotted on silica gel TLC plate, developed with a solvent system of chloroform/methanol/water/formic acid having a 60:40:8:2 volume ratio. The developed TLC plate was sprayed with a 0.2% Wt/Wt ninhydrin solution in ethanol and baked in a 100° C. oven for 5 minutes. The TLC result indicated that most of the starting material had been converted to an amino acid product. The reaction mixture was then centrifuged at 5000 rpm for 30 minutes. The supernatant was concentrated under vacuum to about 40 mL volume, and then adjusted to pH 2.0 with 6N sulfuric acid. The mixture was allowed to stand at 4° C. overnight and then filtered. The filtrate was adjusted to pH 5.4 with 6N NaOH, stirred in an ice bath for 4 hours, and filtered. The solid was recrystallized in acetic acid to obtain 3.6 g L-3-fluorophenylalanine: 1H NMR ($D_2O$) δ 7.65–8.13 (3H, m), 7.58 (1H,m), 4.27 (1H,m), 3.15 (2H,m).

Other variations and modifications of this invention will be obvious to those skilled in the art. This invention is not limited except as set forth in the following claims.

What is claimed:

1. A biocatalytic process to produce optically active phenylalanine analogs from arylacrylic acids, said process comprising the step of combining phenylalanine ammonia-lyase from *Rhodotorula graminis* and ammonia with a compound represented by the formula,

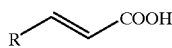

or a salt thereof to generate the optically active amino acid represented by the formula,

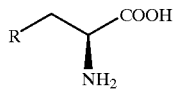

or a salt thereof
wherein R is selected from the group consisting of 2-nitrobenzene 3-nitrobenzene, 3-cyanobenzene, 4-cyanobenzene, 3-phenol, 4-phenol, 1-naphthalene, 2-thiophene, 3-pyridine, 2,3,4,5,6-pentafluorobenzene, 3-chlorobenzene, 2-chlorobenzene, 2,6-dichlorobenzene, 3-bromobenzene, 3-fluorobenzene, 2-fluorobenzene, and 4-fluorobenzene.

2. The biocatalytic process according to claim 1, wherein said *Rhodotorula graminis* is strain ATCC 20804 or a progeny of strain ATCC 20804.

3. The biocatalytic process according to claim 2, wherein said ammonia is aqueous ammonia.

4. The biocatalytic process according to claim 3, further comprising adding a co-solvent, solubilization agent or surfactant to said aqueous ammonia in an amount effective to provide said arylacrylic acid with sufficient solubility to form said optically active amino acid.

5. The biocatalytic process according to claim 1, wherein said arylacrylic acid is pyridylacrylic acid, 3-fluorocinnamic acid, or 3-(2-thienyl)acrylic acid.

6. A biocatalytic process to produce optically active phenylalanine analogs from arylacrylic acids, said process comprising the step of incubating *Rhodotorula graminis* cells in a reaction mixture comprising a compound represented by the formula,

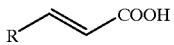

or a salt thereof
and ammonia in an amount effective to generate the optically active amino acid represented by the formula,

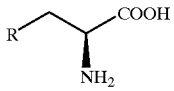

or salt thereof
wherein R is selected from the group consisting of 2-nitrobenzene, 3-nitrobenzene, 3-cyanobenzene, 4-cyanobenzene, 3-phenol, 4-phenol, 1-naphthalene, 2-thiophene, 3-pyridine, 2,3,4,5,6-pentafluorobenzene, 3-chlorobenzene, 2-chlorobenzene, 2,6-dichlorobenzene, 3-bromobenzene, 3-fluorobenzene, 2-fluorobenzene, and 4-fluorobenzene.

7. The biocatalytic process according to claim 6, wherein said *Rhodotorula graminis* is strain ATCC 20804 or a progeny of strain ATCC 20804.

8. The biocatalytic process according to claim 7, wherein said ammonia is aqueous ammonia.

9. The biocatalytic process according to claim 8, wherein said reaction mixture further comprises a co-solvent, or solubilization agent, or surfactant in an amount effective to provide said arylacrylic acid with sufficient solubility to form said optically active amino acid.

10. The biocatalytic process according to claim 9, wherein said solubilization agent is polyethylene glycol.

11. The biocatalytic process according to claim 8, wherein said ammonia is present in an amount from about 5 weight percent to about 45 weight percent of said reaction mixture.

12. The biocatalytic process according to claim 6, wherein said compound is pyridylacrylic acid, 3-fluorocinnamic acid, or 3-(2-thienyl)acrylic acid.

13. The biocatalytic process according to claim 6, further comprising the step of inducing said *Rhodotorula graminis* cells with leucine and isoleucine.

14. The biocatalytic process according to claim 6, wherein said compound is pyridylacrylic acid at a concentration in the range from about 20 g/L to about 100 g/L.

15. The biocatalytic process according to claim 6, wherein said compound is pyridylacrylic acid and the temperature is in the range from about 20° C. to about 45° C.

* * * * *

UNITED STATES PATENT AND TRADEMARK OFFICE
CERTIFICATE OF CORRECTION

PATENT NO. : 5,981,239
DATED : November 9, 1999
INVENTOR(S) : WEIGUO LIU

Page 1 of 2

COVER PAGE:

Line [56] References Cited, under "FOREIGN PATENT DOCUMENTS", "6113870" should read --6-113870--.

COLUMN 3:

Line, 43, "six or" should read --six- or--.

COLUMN 4:

Line 5, "stereo specific" should read --stereospecific--;
Line 14, "was" should read --were--;
Line 15, "was" should read --were--;
Line 35, "as" should read --is as--.

COLUMN 5:

Line 50, "log/L" should read --10g/L--;
Line 59, "preparation" should read --Preparation--.

COLUMN 6:

Line 34, "5 wt. &" should read --5 wt. %--;
Line 52, "i Rhodotorula graminiscells" should read --Rhodotorula graminis cells--.

UNITED STATES PATENT AND TRADEMARK OFFICE
CERTIFICATE OF CORRECTION

PATENT NO.  : 5,981,239
DATED       : November 9, 1999
INVENTOR(S) : WEIGUO LIU

COLUMN 11:

Line 28, "50MG/mL" should read --50 mg/mL--;
Line 59, "herein above," should read --hereinabove,--.

COLUMN 13:

Line 32, "30 35," should read --30, 35,--;
Line 60, "of" should read --for--;
Line 64, "TlC plate" should read --TLC plate--.

COLUMN 14:

Line 7, close up right margin;
Line 8, close up right margin;
Line 24, "of" should read --for--;
Line 65, "2-nitrobenzene" should read --2-nitrobenzene,--.

COLUMN 15:

Line 34, "salt" should read --a salt--.

Signed and Sealed this

Tenth Day of April, 2001

*Attest:*

NICHOLAS P. GODICI

*Attesting Officer*   *Acting Director of the United States Patent and Trademark Office*